United States Patent
Ferriter et al.

(10) Patent No.: US 10,195,344 B2
(45) Date of Patent: Feb. 5, 2019

(54) VALVE PERMITTING MIXING IN A DRUG DELIVERY DEVICE

(71) Applicant: Becton, Dickinson and Company, Franklin Lakes, NJ (US)

(72) Inventors: Matthew Ferriter, Chapel Hill, NC (US); Frank Martin, Durham, NC (US); Vincent J. Sullivan, Cary, NC (US); Scott N. Danhof, Plain City, OH (US); Eric G. Hassenpflug, Westerville, OH (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 592 days.

(21) Appl. No.: 14/443,490

(22) PCT Filed: Nov. 20, 2013

(86) PCT No.: PCT/US2013/070935
§ 371 (c)(1),
(2) Date: May 18, 2015

(87) PCT Pub. No.: WO2014/081785
PCT Pub. Date: May 30, 2014

(65) Prior Publication Data
US 2015/0314071 A1 Nov. 5, 2015

Related U.S. Application Data
(60) Provisional application No. 61/729,824, filed on Nov. 26, 2012.

(51) Int. Cl.
*A61M 5/24* (2006.01)
*A61M 5/28* (2006.01)
(Continued)

(52) U.S. Cl.
CPC .......... *A61M 5/2448* (2013.01); *A61M 5/284* (2013.01); *A61M 5/31596* (2013.01);
(Continued)

(58) Field of Classification Search
CPC ............ A61M 5/19; A61M 2005/1787; A61M 5/2448; A61M 5/284; A61M 5/31596;
(Continued)

(56) References Cited

U.S. PATENT DOCUMENTS 3,108,591 A * 10/1963 Kolbas ................ A61M 5/2448
600/577
4,185,628 A * 1/1980 Kopfer .................. A61M 5/284
222/129
(Continued)

FOREIGN PATENT DOCUMENTS

EP 0397977 A2 11/1990
EP 2042210 A2 1/2009
(Continued)

*Primary Examiner* — Bhisma Mehta
*Assistant Examiner* — William Frehe
(74) *Attorney, Agent, or Firm* — The Webb Law Firm

(57) ABSTRACT

A valve (10) for permitting mixing of at least two components within a barrel (12) is provided including a stopper (20) configured for slidable liquid-tight engagement with an inner surface (13) of the barrel. The stopper is moveable between a first position and a second position and includes a proximal end (22), a distal end (24), and a channel (26) extending therebetween. The valve further includes a stationary body (30) comprising a base (32) and a stem (34), the stem being disposed within the channel of the stopper when the stopper is in the second position. When the stopper is in the first position, there is a liquid-tight seal in the channel, such that fluid flow through the channel is prevented. Movement of the stopper to the second position terminates the liquid-tight seal, thereby establishing fluid communica-
(Continued)

tion through the channel. A drug containing device and assembly for delivering a reconstituted drug are also provided herein.

23 Claims, 6 Drawing Sheets

(51) Int. Cl.
*A61M 5/315* (2006.01)
*A61M 5/178* (2006.01)
*A61M 5/31* (2006.01)

(52) U.S. Cl.
CPC ............... *A61M 2005/1787* (2013.01); *A61M 2005/312* (2013.01); *A61M 2005/3104* (2013.01); *A61M 2005/31598* (2013.01)

(58) Field of Classification Search
CPC .. A61M 2005/311; A61M 2005/31598; A61M 5/285; A61M 5/2455; A61M 39/223
See application file for complete search history.

(56) References Cited

U.S. PATENT DOCUMENTS

| | | |
|---|---|---|
| 4,424,057 A | 1/1984 | House |
| 5,069,670 A | 12/1991 | Vetter et al. |
| 5,102,388 A | 4/1992 | Richmond |
| 5,599,312 A | 2/1997 | Higashikawa |
| 5,704,918 A * | 1/1998 | Higashikawa .......... A61M 5/19 604/191 |
| 7,470,258 B2 | 12/2008 | Barker et al. |
| 2006/0052747 A1 | 3/2006 | Nishimura et al. |
| 2009/0088724 A1 | 4/2009 | Chebator et al. |

FOREIGN PATENT DOCUMENTS

| | | |
|---|---|---|
| JP | 8308928 A | 11/1996 |
| JP | 2001104482 A | 4/2001 |
| JP | 2004147959 A | 5/2004 |
| JP | 2005508656 A | 4/2005 |
| JP | 200982715 A | 4/2009 |
| WO | 02072173 A2 | 9/2002 |

* cited by examiner

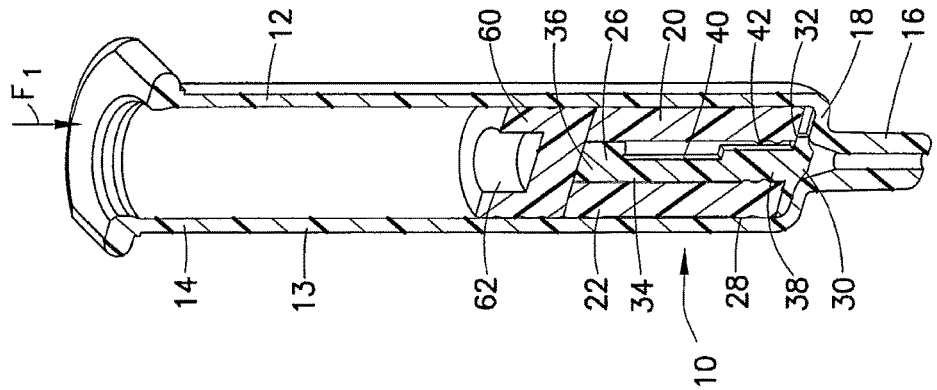
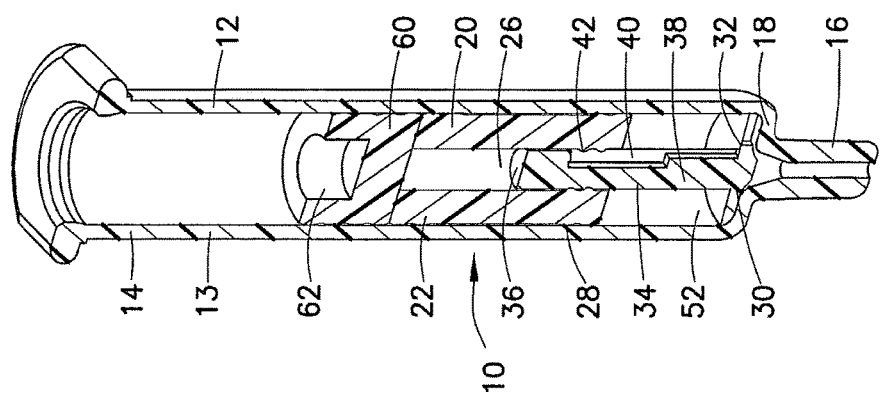
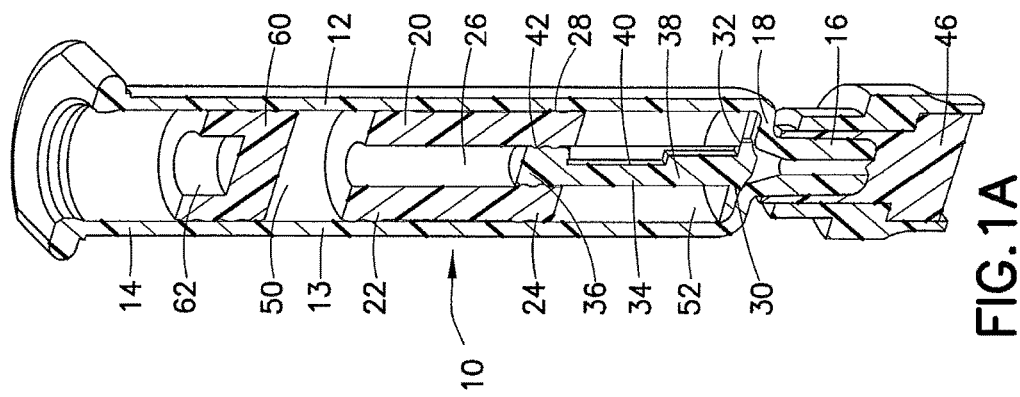

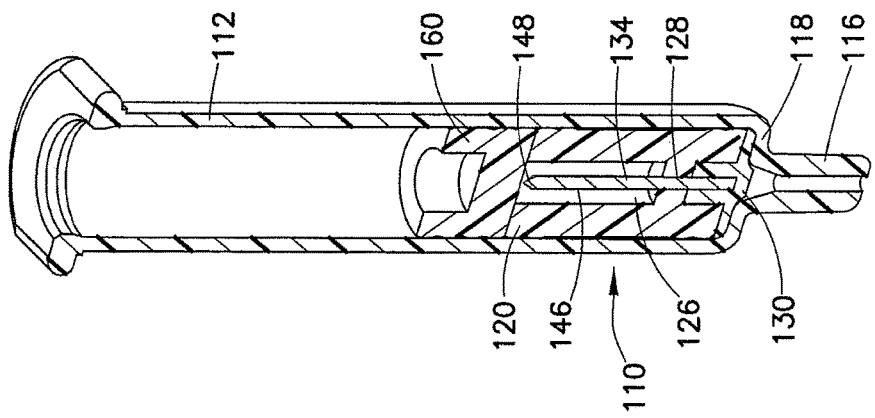
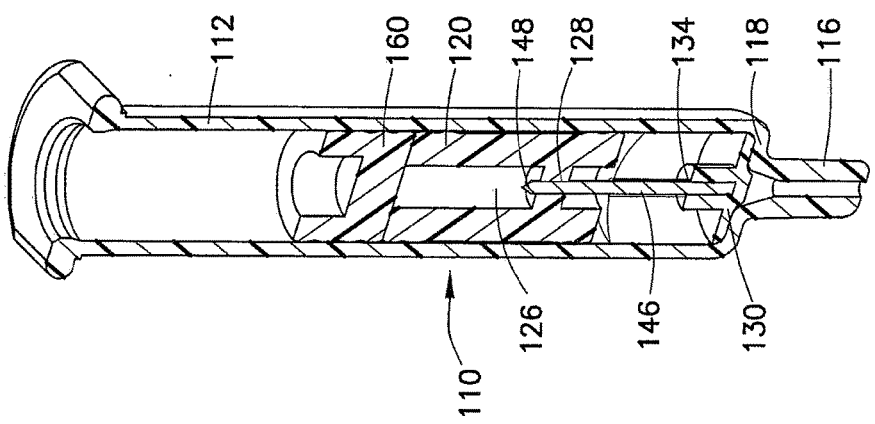
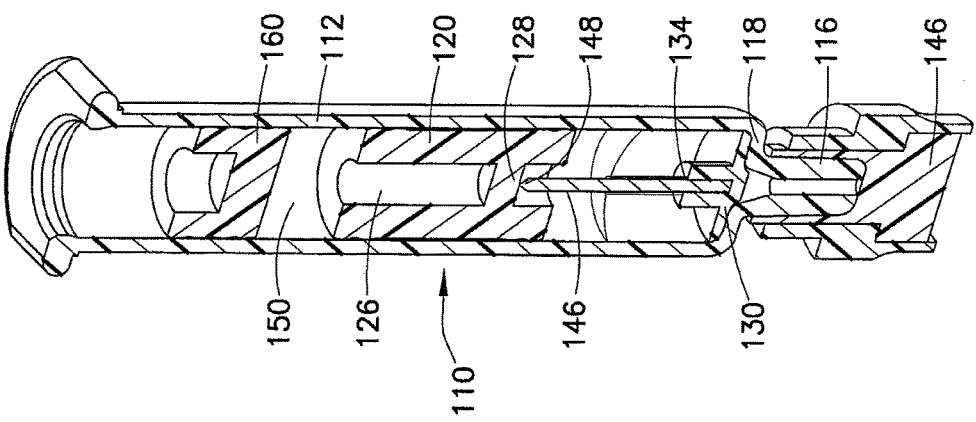

VALVE PERMITTING MIXING IN A DRUG DELIVERY DEVICE

CROSS-REFERENCE TO RELATED APPLICATIONS

This application is the United States national phase of International Application No. PCT/US2013/070935 filed Nov. 20, 2013, and claims priority to U.S. Provisional Application No. 61/729,824 filed Nov. 26, 2012, the disclosures of which are hereby incorporated in their entirety by reference.

BACKGROUND OF THE INVENTION

Field of the Invention

The present invention relates to drug reconstitution devices and, more particularly, to a valve for permitting the mixing of at least two substances within a medical injector or drug cartridge.

Description of Related Art

Certain drugs or medicaments (those terms being used interchangeably herein) are preferably provided in powder or dry form (such as a lyophilized form), and require reconstitution prior to administration. Lyophilized drugs, for example, typically are supplied in a freeze-dried form that needs to be mixed with a diluent to reconstitute the substance into a form that is suitable for injection. Medicaments may also be provided in other dry or powder forms that require reconstitution.

In addition, drugs may be provided as multi-part systems which require mixing prior to administration. For example, one or more liquid (e.g., flowable (slurry or liquid)) components, and/or dry (e.g., powdered or granular) components may be provided in a drug container or delivery device which require mixing prior to administration. Gondatropin and interferon are examples of such multi-component substances which are typically mixed just prior to being administered to a patient.

Prior art devices have been developed that provide a wet component (e.g., liquid) and a dry component (e.g., powder) in separate chambers of a common container with the container being configured to permit the flow of the wet component to the dry component to cause mixing thereof in preparing an administratable solution for injection. The prior devices typically include a bypass channel formed in the container and, as such, the device must be specifically configured for mixing.

Alternatively, prior devices for facilitating the mixing of a wet component and a dry component within a syringe barrel or drug delivery cartridge disclose a valve initially in a closed position which transitions to an open position in response to pressure applied to the valve from the liquid component. Specifically, force from the liquid component overcomes frictional forces between the elements of the valve to open a channel in the valve for the liquid component to pass through. However, these prior valves may fail to open if the frictional engagement between valve elements is too great to be overcome by the fluid force exerted on the valve. In that case, the valve may slip through the barrel instead of opening correctly.

Therefore, there is a need for a reconstitution device which permits mixing of two or more components within a single syringe barrel or drug delivery cartridge and subsequent injection thereof. The cartridge or barrel should not need to be specifically configured for mixing. In addition, the device should have high reliability and, specifically, should not rely on differential frictional forces to transition the valve from a closed to an open position. Finally, the device should have sufficient barrier properties to maintain separation of wet and dry components for long-term storage.

SUMMARY OF THE INVENTION

Provided herein is a valve configured to be received within a syringe barrel or drug delivery cartridge for maintaining prolonged separation between one or more components of a drug to be reconstituted and which allows for mixing of the one or more components within the barrel or injector prior to expulsion of the reconstituted fluid. A drug delivery device including a valve and an expulsion element for propelling a component of the drug to be reconstituted through the valve and for expelling the reconstituted fluid from the device is also provided. Additionally, a drug delivery assembly including a drug delivery device, valve, dry component of a drug to be reconstituted, and wet component of a drug to be reconstituted is also provided.

In accordance with one embodiment of the present invention, a valve for permitting mixing of at least two components within a barrel includes a stopper disposed within the barrel configured for slidable liquid-tight engagement with an inner surface of the barrel. The stopper is moveable between a first position and a second position and includes a proximal end, a distal end, and a channel extending therebetween. The valve further includes a stationary body disposed at least partially within the barrel comprising a base and a stem, the stem being disposed within the channel of the stopper when the stopper is in the second position. When the stopper is in the first position, there is a liquid-tight seal in the channel, such that fluid flow through the channel is prevented. Movement of the stopper to the second position terminates the liquid-tight seal, thereby establishing fluid communication through the channel and defining a liquid flow path from the proximal end of said stopper to a distal end of the barrel. The base of the body may sit on an internal shoulder located at the distal end of the barrel.

In certain configurations, the stopper includes a pierceable septum located in the channel of the stopper which creates the liquid-tight seal. Further, a proximal portion of the stem may have a tip for piercing the pierceable septum when the stopper is moved to the second position.

In other configurations, at least a portion of the stem is disposed within the channel of the stopper in the first position and engages with the channel to form the liquid-tight seal. Further, the stem of the body may further include a port extending from the proximal end of the stem to the base for permitting fluid flow from the channel of the stopper to a distal portion of the barrel according to the liquid flow path when the stopper is in the second position. Additionally, the proximal end of the channel has a larger diameter than the distal end of the channel, such that movement of the stopper to the second position disengages the stem from the channel and advances the stem farther within the channel.

In accordance with another embodiment of the present invention, a drug containing device includes a barrel having a proximal end and a distal end and a valve disposed in said barrel. The valve includes a stopper disposed within the barrel configured for slidable liquid-tight engagement with an inner surface of the barrel and moveable between a first position and a second position, the stopper having a proximal end, a distal end, and a channel extending therebetween and a stationary body disposed at least partially within the barrel comprising a base and a stem, the stem being disposed within the channel of the stopper when the stopper is in the second position. When the stopper is in the first position, there is a liquid-tight seal in the channel, such that fluid flow through the channel is prevented. Movement of the stopper to the second position terminates the liquid-tight seal, thereby establishing fluid communication through the channel and defining a liquid flow path from the proximal end of said stopper to a distal end of the barrel. The barrel may include an inner shoulder located on the distal end of the barrel. The base of the body may sit on the inner shoulder of the barrel.

In certain configurations, the stopper includes a pierceable septum located in the channel of the stopper which creates the liquid-tight seal. Further, a proximal portion of the stem may have a tip for piercing the pierceable septum when the stopper is moved to the second position.

In other configurations, at least a portion of the stem is disposed within the channel of the stopper in the first position and engages with the channel to form the liquid-tight seal. Further, the stem of the body may further include a port extending from the proximal end of the stem to the base for permitting fluid flow from the channel of the stopper to a distal portion of the barrel, according to the liquid flow path when the stopper is in the second position. Additionally, the proximal end of the channel has a larger diameter than the distal end of the channel, such that movement of the stopper to the second position disengages the stem from the channel and advances the stem farther within the channel.

The drug containing device may be an injector or may be a drug delivery cartridge.

In accordance with another embodiment of the present invention, an assembly is provided including a drug delivery device comprising a barrel and a valve. The valve includes a stopper disposed within the barrel configured for slidable liquid-tight engagement with an inner surface of the barrel and moveable between a first position and a second position, the stopper having a proximal end, a distal end, and a channel extending therebetween and a stationary body disposed at least partially within the barrel comprising a base and a stem, the stem being disposed within the channel of the stopper when the stopper is in the second position. When the stopper is in the first position, there is a liquid-tight seal in the channel, such that fluid flow through the channel is prevented. Movement of the stopper to the second position terminates the liquid-tight seal, thereby establishing fluid communication through the channel and defining a liquid flow path from the proximal end of said stopper to a distal end of the barrel. The assembly further includes a dry component disposed within said barrel distally of said valve and a liquid component for reconstituting said dry component disposed within said barrel proximally of said valve.

In certain configurations, the assembly further includes a plunger disposed initially in the proximal end of the barrel, wherein advancing the plunger toward the distal end of the barrel causes the stopper to move distally from the first position to the second position. Optionally, continued distal movement of the plunger advances the stopper to a third position in which the stopper abuts the base of the body thereby causing the reconstituted dry and liquid components to be expelled from a nozzle located at the distal end of the barrel.

In accordance with another embodiment of the present invention, a valve for permitting mixing of at least two components within a barrel includes a moveable stopper disposed within the barrel configured for slidable liquid-tight engagement with the inner surface of the a barrel having a proximal end, a distal end, and a channel extending therebetween. The valve further includes a removable cap comprising a base and a pin, the pin having a distal end connected to the base and a proximal end disposed within the fluid channel of the stopper. When the stopper is in a first position, the stem of the cap forms a liquid-tight seal in the channel of the stopper such that fluid flow through the channel is prevented. When the cap is removed from the barrel, fluid communication through the fluid channel is established, thereby defining a liquid flow path from the proximal end of said stopper to a distal end of the barrel.

BRIEF DESCRIPTION OF THE DRAWINGS

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

FIG. 1A is a cross-sectional perspective view of a valve for reconstitution disposed within a syringe barrel and configured in the first or storage position in accordance with an embodiment of the present invention.

FIG. 1B is a cross-sectional perspective view of the valve of FIG. 1A in the second or mixed position in accordance with an embodiment of the present invention.

FIG. 1C is a cross-sectional perspective view of the valve of FIG. 1A in the third position in accordance with an embodiment of the present invention.

FIG. 3A is a cross-sectional perspective view of a valve for reconstitution disposed within a syringe barrel and configured in the first or storage position in accordance with a second embodiment of the present invention.

FIG. 3B is a cross-sectional perspective view of the valve of FIG. 3A in the second or mixed position in accordance with an embodiment of the present invention.

FIG. 3C is a cross-sectional perspective view of the valve of FIG. 3A in the third position in accordance with an embodiment of the present invention.

DESCRIPTION OF THE PREFERRED EMBODIMENTS

Figure 1D:
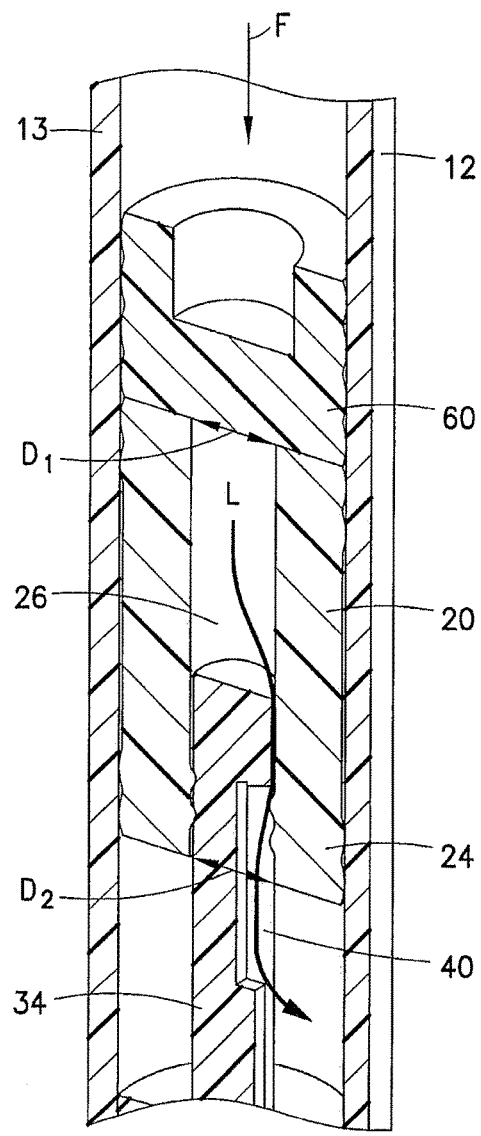
FIG. 1D is an enlarged partial cross-sectional perspective view of the valve of FIG. 1A in the second position showing liquid flow through the stopper in accordance with an embodiment of the present invention.

For the purpose of facilitating understanding of the invention, the accompanying drawings and description illustrate preferred embodiments thereof, from which the invention, various embodiments of its structures, construction and method of operation, and many advantages may be understood and appreciated.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

With reference to FIGS. 1A-1C, a valve 10 is shown for permitting mixing of at least two components. As further discussed below, the valve 10 is particularly well-suited for use with reconstitution of one or more drugs in which one component is a wet (e.g., liquid) component suitable for reconstituting a dry (e.g., lyophilized powder) component. The valve 10 may be used and disposed within a barrel of an injector (i.e., a medical injector), such as a syringe or pen injector, or in the barrel of a drug cartridge.

As depicted in FIG. 1A, a barrel 12 may be in the general form of an elongated cylindrical barrel, although other forms for containing a fluid for delivery are also contemplated by the present invention. Additionally, the barrel 12 may be formed of glass, or may be injection molded from thermoplastic material such as polypropylene and polyethylene according to techniques known to those of ordinary skill in the art, though it is to be appreciated that the barrel 12 may be made from other suitable materials and according to other applicable techniques. The barrel 12 may include markings, such as graduations on the wall thereof, for providing an indication as to the level or amount of fluid contained within the barrel. Such markings may be provided on the external wall, the internal wall, or integrally formed or otherwise within the wall of the barrel 12. Alternatively, or in addition thereto, the markings may provide a description of the contents of the syringe, or other identifying information, as may be known in the art. Holding shoulders 18, formed by the sidewalls of a nozzle 16, are located at the distal end of the barrel 12.

As will be recognized by those skilled in the art, the valve 10 may be used to permit mixing of various components, such as one or more wet components, which may be in any flowable form, such as in a liquid, syrup, or slurry form, and/or one or more dry components, which may be in powder or granular form.

With reference to FIGS. 1A-2B, the valve 10 generally includes a stopper 20 and a body 30. The stopper 20 is configured to be in sliding liquid-tight engagement with the interior of a sidewall 13 of the barrel 12. The stopper 20 may be formed of an elastomeric material, and may include a proximal end 22, a distal end 24, and a channel 26 defined therein and extending at least partially therebetween. In one non-limiting embodiment of the invention, the channel 26 defines a larger diameter $D_1$ at the proximal end 22 of the stopper 20 and a smaller diameter $D_2$ at the distal end 24. One or more ribs 28 may be formed circumferentially about the stopper 20 to enhance the integrity of the liquid-tight seal formed between the stopper 20 and the barrel 12. The stopper 20 is moveable within the barrel 12 from a first or storage position (see FIG. 1A), to a mixing or second position (see FIG. 1B), to a dispersal or third position (see FIG. 1C).

Figure 2A:
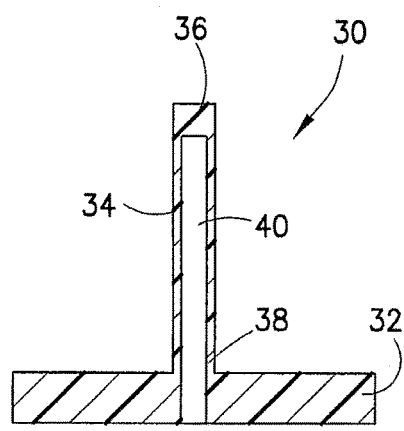
FIG. 2A is a side view of the valve body of the valve of FIG. 1A in accordance with an embodiment of the present invention.

With reference now to FIG. 2A, the body 30 of the valve 10 generally includes a base 32 and a stem 34 connected to the base 32. The base 32 may be formed of various materials, including rigid plastics, and may be manufactured using, among other techniques, injection molding. In one embodiment, the base 32 is restrained by holding shoulders 18, as shown in FIGS. 1A-1C. The stem 34 may also be formed from rigid plastics or, alternatively, from metal. In certain configurations, the base 32 and the stem 34 may be co-formed. The stem 34 includes a proximal end 36 and a distal end 38. The proximal end 36 is adapted to be disposed within the channel 26 of the stopper 20. The distal end 38 is connected to the base 32. In one embodiment, the stem 34 extends from the base 32 in a substantially perpendicular orientation. The stem 34 further includes a port 40 extending longitudinally along at least a portion of the stem 34.

Figure 2B:
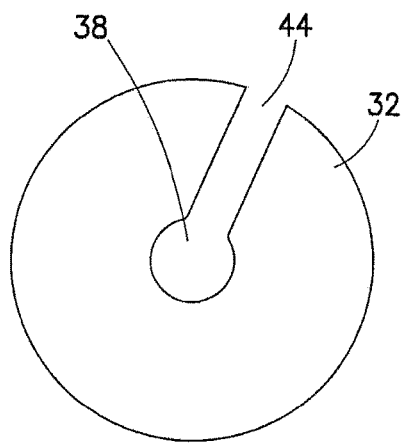
FIG. 2B is a bottom view of the valve body of the valve of FIG. 1A in accordance with an embodiment of the present invention.
Figure 3D:
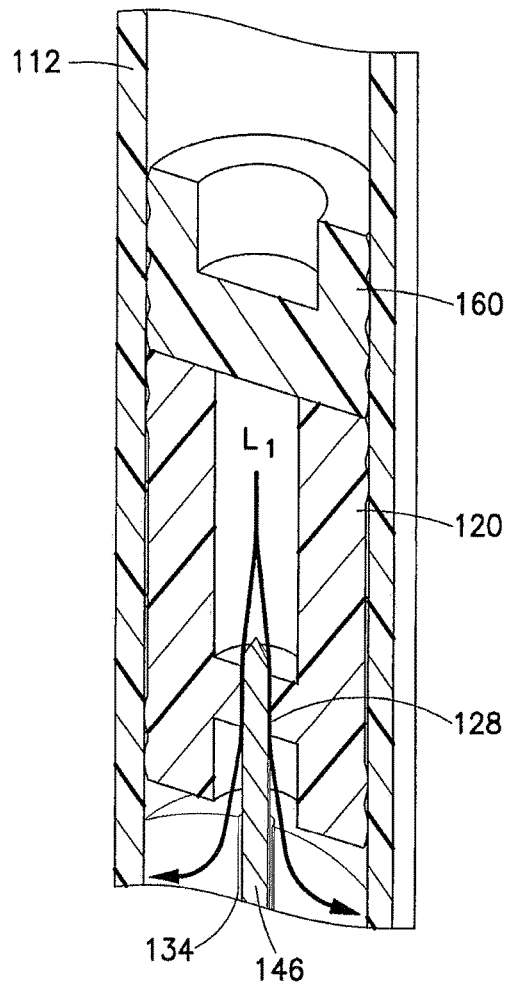
FIG. 3D is an enlarged partial cross-sectional perspective view of the valve of FIG. 3A in the second position showing liquid flow through the stopper in accordance with an embodiment of the present invention.

In the first position, as shown in FIG. 1A, a liquid-tight seal is formed within the channel 26 to prevent fluid flow through the channel 26. According to one non-limiting embodiment of the invention, the liquid-tight seal is formed as a result of engagement between the stem 34 of the body 30 and channel 26 of the stopper 20. As depicted in FIG. 1A, the entirety of the port 40 is located distally from the stopper 20 in the first position. Thus, the port 40 is not disposed within the channel 26 of the stopper 20 in the first position. To enhance the integrity of the liquid-tight seal, one or more sealing ribs 42 may be defined on the proximal end 36 of the stem 34 and/or may extend from the inner surface of the channel 26. As depicted in FIG. 2B, the base 32 further includes a slit 44 extending radially outward from the central portion of the base. The slit 44 allows fluid to pass through the base 32 to be expelled from the barrel 12 through the nozzle 16.

In use, the valve 10 is disposed within the interior of the barrel 12 separating the barrel 12 into a first chamber 52 and a second chamber 50. The first chamber 52 may be distal to the valve 10 and the second chamber 50 may be proximal to the valve 10. A dry component, such as a dry medicament, may be provided within the first chamber 52 and a wet component, such as a liquid suitable for reconstituting the dry component, may be disposed within the second chamber 50. With reference to FIG. 1A, the valve 10 is initially in a closed position. In the closed position, the stem 34 defines the liquid-tight seal in the channel 26, such that liquid flow L (FIG. 1D) through the channel 26 is prevented. In addition, the liquid-tight seal defined between the stopper 20 and the barrel 12 prevents liquid flow about the stopper 20. Therefore, the dry component housed in the first chamber 52 may be maintained in a dry state during storage or transportation.

When ready for use, pressure is applied to the wet component housed in the second chamber 50 in any known manner, including through a manual or automatic application of force. With reference to FIG. 1A, in one non-limiting embodiment of the present invention, pressure is applied by a plunger 60 disposed within the barrel 12 located at a proximal position relative to the wet component housed in the second chamber 50. The plunger 60 may optionally be connected to a plunger rod (not shown) at a connection joint 62. The connection joint 62 may be configured so that the plunger rod screws into the plunger 60. Applying downward force to the plunger 60 in the direction of arrow F, as shown in FIG. 1D, distally advances the plunger 60 through the barrel 12.

With the fluid component housed in second chamber 50 being incompressible or generally incompressible, the applied pressure is transmitted through the fluid component to the stopper 20. The applied force causes the stopper 20 to move distally through the barrel 12 while the body 30 remains stationary. With the proximal portion of the channel 26 having a larger diameter than the distal portion, the stem 34, which initially defines the liquid-tight seal with the channel 26, comes out of engagement with the channel 26. Continued distal movement of the stopper 20 brings the stem 34 further into the channel 26, thereby establishing fluid communication through the channel 26 of the stopper 20 and port 40 of the stem 34. As such, a liquid flow path L (FIG. 1D) is defined through the channel 26 and port 40.

With continued reference to FIG. 1B, under further application of pressure, the valve 10 is fixed relative to the barrel 12 due to the frictional resistance against movement generated at the interface between the stopper 20 and the barrel 12. At this point the fluid component housed within second chamber 50 is forced through the channel 26 and port 40 according to liquid flow path L, as shown in FIG. 1D. The liquid component housed within second chamber 50 is forced through channel 26 and port 40 to enter the first chamber 52 housing the dry component. In this way, the liquid component housed in second chamber 50 is reconstituted with the dry component housed in first chamber 52 producing a solution which is ready for injection. The solution may include a pharmaceutically active agent.

With reference now to FIG. 1C, once the liquid component housed in first chamber 52 is forced through the stopper channel 26, the plunger 60 is brought into abutting engagement with the proximal end 22 of the stopper 20. Continued application of force in the direction of arrow F, as shown in FIG. 1C, moves the plunger 60 and stopper 20 through the barrel 12 in the distal direction toward the reconstituted fluid. The reconstituted fluid is then dispersed from the barrel 12 by passing through the slit 44 of the base 32 and through the nozzle 16.

The valve 10 may be used in similar manner to mix one or more wet components, e.g., wet components being located on both sides of the valve 10. A series of the valves 10 may also be used to allow for mixing of a plurality of wet and/or dry components.

Figure 4A:
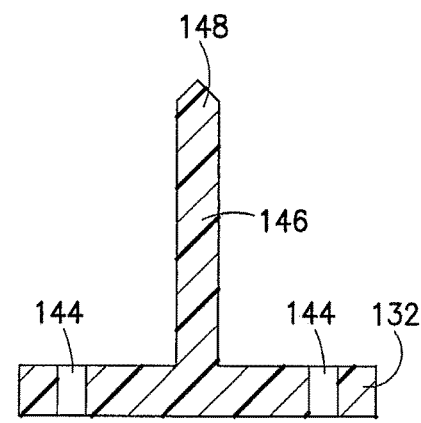
FIG. 4A is a side view of the valve body of the valve of FIG. 3A in accordance with an embodiment of the present invention.
Figure 4B:
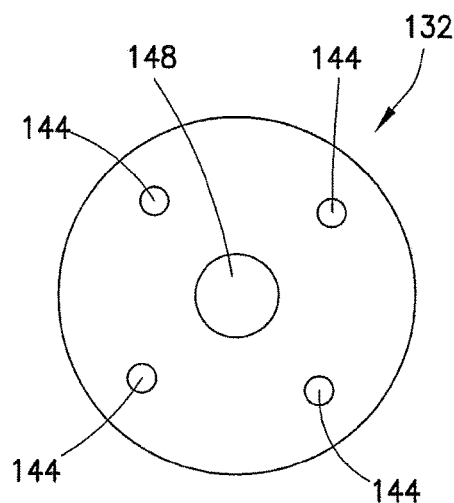
FIG. 4B is a bottom view of the valve body of the valve of FIG. 3A in accordance with an embodiment of the present invention.

With reference now to FIGS. 3A-4B, a valve 110 is similarly presented according to another non-limiting embodiment of the present invention. In this embodiment, a stem 134 of a body 130 comprises a needle 146 having a tip 148. The tip 148 is adapted to engage with a pierceable septum 128 of a stopper 120. A base 132 further includes a plurality of dispersion ports 144, as shown in FIG. 4B, for allowing the reconstituted fluid to pass through the base 132 for dispersal from a barrel 112. As in the embodiment of the invention described above with reference to FIGS. 1A-2B, the base 132 is restrained by holding shoulders 118 of the barrel 112.

In the first position (see FIG. 3A), the pierceable septum 128 forms the liquid-tight seal within a channel 126. As with the embodiment described above with reference to FIGS. 1A-2B, when ready for use, pressure is applied to the liquid component housed in a second chamber 150, through any known means including driving a plunger 160 through the barrel 112, causing the stopper 120 to descend distally through the barrel 112. The body 130 and, specifically, the stem 134 remain stationary. The distal movement of the stopper 120 brings the pierceable septum 128 into contact with the tip 148 of the needle 146 of the stem 134. Further pressure pierces the septum 128 establishing a liquid flow path $L_1$ (see FIG. 3D) through the stopper 120.

With continued reference to FIG. 3B, further application of pressure forces the fluid component housed within second chamber 150 through the stopper 120, thereby introducing the liquid component to the dry component housed within a first chamber 152 for reconstitution. The reconstituted fluid is dispersed through a nozzle 116 in the same manner as described for the previous embodiment of the invention.

Figure 5C:
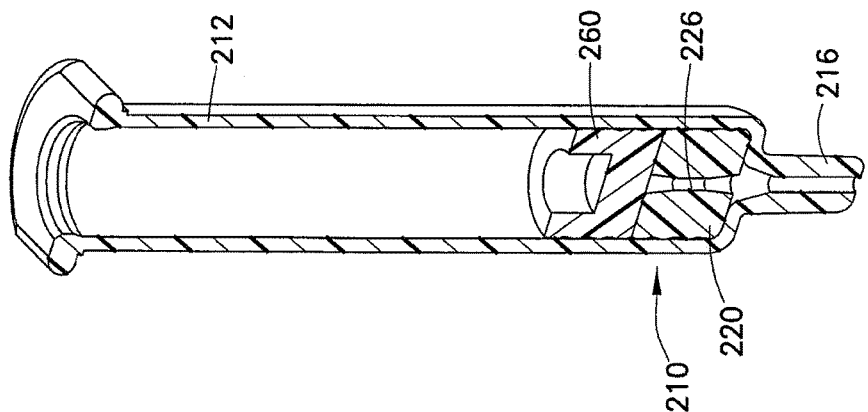
FIG. 5C is a cross-sectional perspective view of the valve of FIG. 5A in the third position in accordance with an embodiment of the present invention.
Figure 5B:
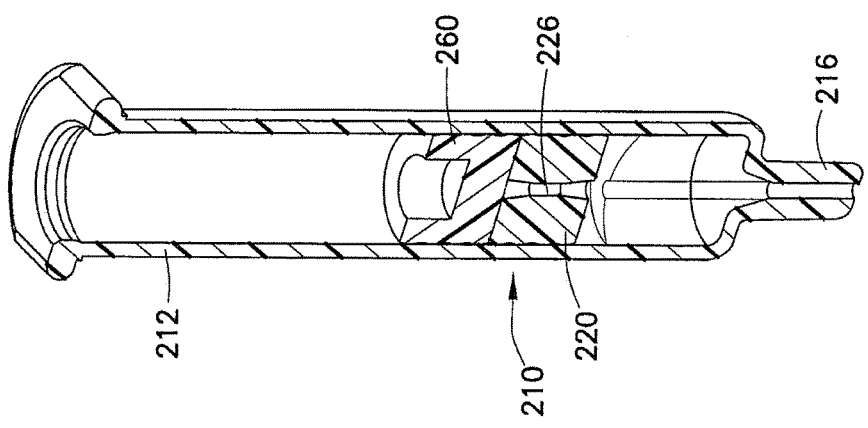
FIG. 5B is a cross-sectional perspective view of the valve of FIG. 5A in the second or mixed position in accordance with an embodiment of the present invention.
Figure 5A:
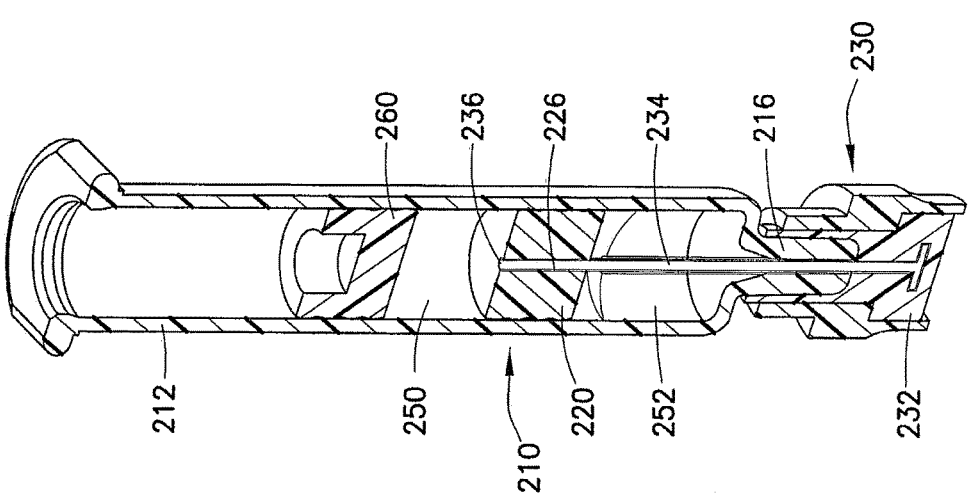
FIG. 5A is a cross-sectional perspective view of a valve for reconstitution disposed within a syringe barrel and configured in the first or storage position in accordance with a third embodiment of the present invention.
Figure 6:
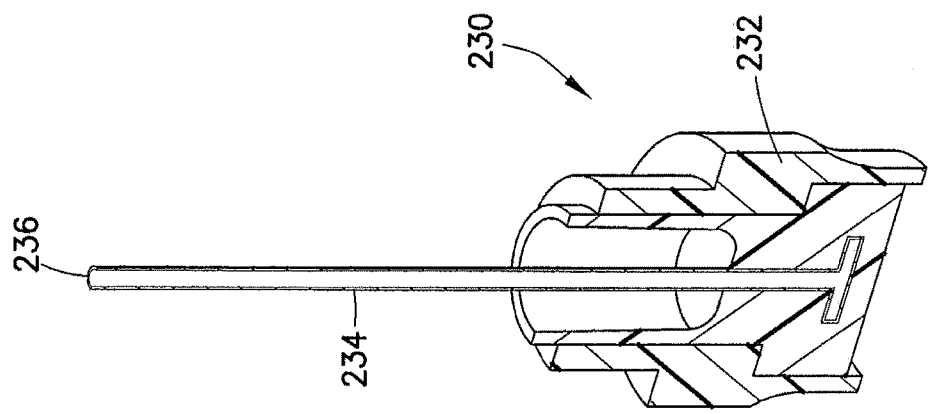
FIG. 6 is a partial cross-sectional perspective view of a portion of the cap of the valve of FIG. 5A in accordance with an embodiment of the present invention.
Figure 5D:
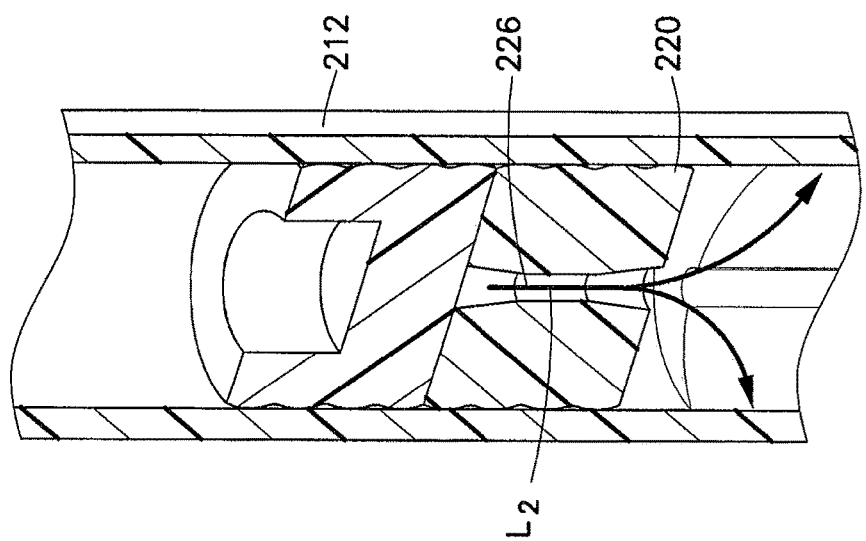
FIG. 5D is an enlarged partial cross-sectional perspective view of the valve of FIG. 5A in the second position showing liquid flow through the stopper in accordance with an embodiment of the present invention.

With reference to FIGS. 5A-6, a further non-limiting embodiment of a valve 210 of the present invention is depicted. The valve 210 comprises a stopper 220 and a removable cap 230. The cap 230 includes a base 232 and a stem 234. In the initial position (see FIG. 5A), the base 232 is located outside a barrel 212. The stem 234 extends into the barrel 212 through the nozzle 216, such that a proximal end 236 of the stem 234 is disposed within a channel 226 of the stopper 220 forming a liquid-tight seal. When ready for use, a user removes the cap 230, thereby removing the stem 234 from the channel 226 to establish fluid communication through the channel 226 of the stopper 220 along liquid flow path $L_2$ (see FIG. 5D). Application of pressure to the liquid component housed within a second chamber 250 forces the liquid component through the channel 226, along path $L_2$, thereby forcing the liquid component into first chamber 252 housing the dry component for reconstitution. Continued application of pressure advances the stopper 220 distally through the barrel 212, thereby dispensing the reconstituted fluid from the barrel 212 through the nozzle 216 in the same manner as described above for previous embodiments of the invention.

What is claimed is:
1. A valve for permitting mixing of at least two components within a medical barrel comprising:
   a stopper disposed within the barrel configured for slidable engagement with an inner surface of the barrel and moveable between a first position and a second position, the stopper having a proximal end, a distal end, and a channel extending therebetween; and
   a stationary body disposed at least partially within the barrel comprising a base and a stem, the stem being disposed within the channel of the stopper when the stopper is in the second position, the stationary body comprising a sealing portion at a proximal end of the stem, the sealing portion having a first cross section, the stationary body further comprising at least one narrow portion distal to the sealing portion, the at least one narrow portion having a second cross section, which is smaller than the first cross section,
   wherein when the stopper is in the first position, the sealing portion of the stationary body seals against an inner surface of the channel, such that fluid flow through the channel is prevented, and wherein movement of the stopper from the first position to the second position, such that the sealing portion of the stationary body moves proximally through at least a portion of the channel of the stopper, forms a flow path between an outer surface of the at least one narrow portion of the stationary body and the inner surface of the channel to establish fluid communication through the channel.

2. The valve of claim 1, wherein the at least two components include at least one liquid component and at least one dry component.

3. The valve of claim 1, wherein the stopper comprises a pierceable septum extending across the inner surface of the channel blocking fluid flow through the channel.

4. The valve of claim 3, wherein the proximal end of the stem further comprises a tip for piercing the pierceable septum when the stopper is moved to the second position.

5. The valve of claim 1, wherein the stem is disposed within the channel of the stopper in the first position and cooperates with the channel to form a liquid-tight seal therewith.

6. The valve of claim 1, wherein the channel includes a proximal end having a first diameter, and a distal end having a second diameter, wherein the first diameter is larger than the second diameter.

7. A drug containing device comprising:
a barrel having a proximal end and a distal end;
a valve disposed in said barrel, said valve including:
a stopper disposed within the barrel configured for slidable engagement with an inner surface of the barrel and moveable between a first position and a second position, the stopper having a proximal end, a distal end, and a channel extending therebetween; and
a stationary body disposed at least partially within the barrel comprising a base and a stem, the stem being disposed within the channel of the stopper when the stopper is in the second position, the stationary body comprising a sealing portion at a proximal end of the stem, the sealing portion having a first cross section, the stationary body further comprising at least one narrow portion distal to the sealing portion, the at least one narrow portion having a second cross section, which is smaller than the first cross section,
wherein when the stopper is in the first position, the sealing portion of the stationary body seals against an inner surface of the channel, such that fluid flow through the channel is prevented, and
wherein movement of the stopper from the first position to the second position, such that the sealing portion of the stationary body moves proximally through at least a portion of the channel of the stopper, forms a flow path between an outer surface of the at least one narrow portion of the stem and an inner surface of the channel to establish fluid communication through the channel.

8. The device of claim 7, wherein the barrel further includes a holding shoulder adjacent the distal end of the barrel, and wherein the base of the stationary body contacts the holding shoulder of the barrel.

9. The device of claim 7, wherein the valve is configured for mixing at least two components within the barrel.

10. The device of claim 9, wherein the at least two components include at least one liquid component and at least one dry component.

11. The device as in claim 7, wherein the stopper comprises a pierceable septum extending across the inner surface of the channel blocking fluid flow through the channel.

12. The device of claim 7, wherein the proximal end of the stem further comprises a tip for piercing the pierceable septum when the stopper is moved to the second position.

13. The device of claim 7, wherein the stem is disposed within the channel of the stopper in the first position and cooperates with the channel to form a liquid-tight seal therewith.

14. The device of claim 7, wherein the stem comprises a port extending from the proximal end of the stem to the base, and wherein the flow path passes through the port for permitting fluid flow from the channel of the stopper to the distal end of the barrel when the stopper is in the second position.

15. The device of claim 7, further comprising a plunger disposed initially in the proximal end of the barrel wherein advancing the plunger toward the distal end of the barrel causes the stopper to move distally from the first position to the second position.

16. The device of claim 15, wherein continued distal movement of the plunger advances the stopper to a third position in which the stopper abuts the base of the stationary body.

17. The device of claim 7, wherein the device is an injector.

18. The device of claim 7, wherein the device is a drug cartridge.

19. An assembly comprising:
a drug delivery device comprising:
a barrel having a proximal end and a distal end;
a valve disposed in said barrel, said valve including:
a stopper disposed within the barrel configured for slidable engagement with an inner surface of the barrel and moveable between a first position and a second position, the stopper having a proximal end, a distal end, and a channel extending therebetween; and
a stationary body disposed at least partially within the barrel comprising a base and a stem, the stem being disposed within the channel of the stopper when the stopper is in the second position, the stationary body comprising a sealing portion at a proximal end of the stem, the sealing portion having a first cross section, the stationary body further comprising at least one narrow portion distal to the sealing portion, the narrow portion having a second cross section, which is smaller than the first cross section,
wherein when the stopper is in the first position, the sealing portion of the stationary body seals against an inner surface of the channel, such that fluid flow through the channel is prevented, and
wherein movement of the stopper from the first position to the second position, such that the sealing portion of the stationary body moves proximally through at least a portion of the channel of the stopper, forms a flow path between an outer surface of the narrow portion of the stem and the inner surface of the channel to establish fluid communication through the channel;
a dry component disposed within the barrel distally of the valve; and
a liquid component for reconstituting the dry component disposed within the barrel proximally of the valve.

20. The assembly of claim 19, further comprising a plunger disposed initially in the proximal end of the barrel, wherein advancing the plunger toward the distal end of the barrel causes the stopper to move distally from the first position to the second position.

21. The assembly of claim 20, wherein continued distal movement of the plunger advances the stopper to a third position in which the stopper abuts the base of the stationary body, thereby causing the reconstituted dry and liquid components to be expelled from a nozzle located at the distal end of the barrel.

22. The assembly of claim 19, wherein the device is an injector.

23. The assembly of claim 19, wherein the device is a drug cartridge.

* * * * *

UNITED STATES PATENT AND TRADEMARK OFFICE
CERTIFICATE OF CORRECTION

PATENT NO. : 10,195,344 B2
APPLICATION NO. : 14/443490
DATED : February 5, 2019
INVENTOR(S) : Matthew Ferriter et al.

Page 1 of 1

It is certified that error appears in the above-identified patent and that said Letters Patent is hereby corrected as shown below:

In the Claims

Column 9, Line 57, Claim 7, delete "an" and insert -- the --

Signed and Sealed this
Twenty-third Day of April, 2019

Andrei Iancu
*Director of the United States Patent and Trademark Office*